United States Patent [19]

Kuck et al.

[11] 4,338,166

[45] Jul. 6, 1982

[54] ELECTROCHEMICAL SYNTHESIS OF ORGANOPHOSPHORUS COMPOUNDS

[75] Inventors: Mark A. Kuck, Upper Montclair, N.J.; Gary K. Miller, Port Chester, N.Y.

[73] Assignee: Stauffer Chemical Company, Westport, Conn.

[21] Appl. No.: 213,774

[22] Filed: Dec. 8, 1980

[51] Int. Cl.$^3$ .......................... C01B 25/00; C25B 3/00
[52] U.S. Cl. .............................. 204/59 R; 204/59 QM
[58] Field of Search .................. 204/59 R, 72, 59 QM

[56] References Cited

U.S. PATENT DOCUMENTS

| | | | |
|---|---|---|---|
| 3,730,857 | 5/1973 | Tripp | 204/59 QM |
| 3,730,864 | 5/1973 | Tarjanyi et al. | 204/149 |
| 4,250,000 | 2/1981 | Kuck et al. | 204/59 QM |

FOREIGN PATENT DOCUMENTS 2121732  3/1972  Fed. Rep. of Germany .... 204/59 R

*Primary Examiner*—Howard S. Williams
*Attorney, Agent, or Firm*—Henry Z. Friedlander

[57] ABSTRACT

A process for the preparation of organophosphorus derivatives of organic hydroxyl or sulfhydryl compounds which includes the step of electrolyzing said organic hydroxyl or sulfhydryl compounds in an electrochemical cell having an anode comprising ferrophosphorus.

10 Claims, No Drawings

ELECTROCHEMICAL SYNTHESIS OF ORGANOPHOSPHORUS COMPOUNDS

BACKGROUND OF THE INVENTION

This invention relates to organophosphorus compounds, especially organophosphates and organothiophosphates. More particularly, it relates to the electrochemical synthesis of organophosphates and organothiophosphates in compartmented or uncompartmented cells at ambient temperature and pressure.

Neutral organic esters and thioesters of phosphoric acid have been synthesized in the past by the reaction of phosphorus trichloride and phosphorus oxychloride with alcohols, phenols, mercaptans, or thiophenols. More recently organic phosphates have been prepared by the reaction of phosphorus pentachloride with ethers, as disclosed in U.S. Pat. No. 2,407,279. Employing phosphorus halides to make organic phosphates or thiophosphates generates hydrogen halides as by-products, which are corrosive, difficult to handle, and troublesome to dispose of in an environmentally sound manner. The reaction of phosphorus pentoxide with organic hydroxyl or sulfhydryl compounds requires high temperatures, often high pressure, and the maintenance of supplies of reactive chemicals in inventory.

Warshawsky, Tomilov, and Smirnov published in the All-Union Journal of General Chemistry 7, 598 (1962-USSR) a description of an electrochemical process for the synthesis of trialkyl phosphates by passing current between graphite electrodes in a cell containing alcoholic hydrogen chloride and a suspension of red phosphorus. Trimethyl, triethyl, tributyl and triamyl phosphates were made from the respective alcohols by this procedure.

Fraser in U.S. Pat. No. 2,133,290 of 1938 disclosed a process for making iron oxide and sodium phosphate in an electrolytic cell with a ferrophosphorus anode, a graphitic or lead cathode, and a concentrated aqueous caustic electrolyte.

In U.S. Pat. No. 2,173,103 of 1939 Fraser disclosed a process for making iron phosphate in an electrolytic cell with a ferrophosphorus anode, a graphitic or lead cathode, and a concentrated aqueous solution of an alkali metal salt plus, optionally, alkali metal hydroxide as the electrolyte.

In U.S. Pat. No. 3,730,864 of 1973 Tarjanyi disclosed a process for decreasing the phenolic content of dilute aqueous solutions electrochemically by passing current through a cell packed 40-80% by volume with a bed of particles in the electrolyte. One of the numerous types of particles which Tarjanyi discloses for the electrolytic bed is ferrophosphorus, which is not named as a possible electrode, however.

A principal object of the invention is to produce organophosphorus compounds directly from ferrophosphorus. Another object of the invention is to utilize ferrophosphorus, a by-product of the winning of elemental phosphorus from phosphate rock. Still another object of the invention is to produce trialkyl phosphates and thiophosphates without generating hydrogen chloride as a by-product. A further object of the invention is to produce organophosphorus compounds at ambient temperatures and pressures. Other objects of the invention will be evident to those skilled in the art from study of the description and examples below.

SUMMARY OF THE INVENTION

Surprisingly, it has been found that electrolysis of alcohols, phenols, mercaptans, and thiophenols made conductive by the presence of an inorganic salt in a cell equipped with an anode of ferrophosphorus leads to the production of organophosphorus compounds in the electrolyte. Electrolysis of alcohols primarily produces trialkyl phosphates. The product from phenols in the electrolyte is triaryl phosphates. Sulfhydryl compounds yield thioesters. Polyhydric compounds such as ethylene glycol may also be employed.

DESCRIPTION OF THE INVENTION

Elemental phosphorus is produced commercially from phosphate rock in an electrically heated furnace by reduction with coke in the presence of sand. In the course of this reduction iron impurities from all sources, including the furnace, react with phosphorus to produce ferrophosphorus, which is tapped off from the furnace below the silicate slag. For each kilogram of elemental phosphorus product, approximately 0.3 kg ferrophosphorus is made. The main use of ferrophosphorus is in steel making where about 0.1 percent phosphorus in the steel is considered advantageous. Other applications for ferrophosphorus by-product would be desirable.

Ferrophosphorus compounds with formulae, $FeP_2$, $FeP$, $Fe_2P$, and $Fe_3P$ are known and have been characterized. All the ferrophosphides are good conductors of electricity, and therefore can serve as electroconductive sources of phosphorus. Ferrophosphides with a phosphorus content of from about 22 to about 30 weight percent phosphorus are preferred as anodes in the present invention.

Two commercial samples of ferrophosphorus employed as anodes in the examples described below, designated MP and SB, had the following elemental analysis corresponding to $Fe_2P$:

| Element | Wgt. % in Sample MP | Wgt. % in Sample SB |
| --- | --- | --- |
| Phosphorous | 26.2 | 26.9 |
| Iron | 66.3 | 61.0 |
| Chromium | 1.0 | 3.92 |
| Vanadium | 0.2 | 6.05 |
| Silicon | 0.32 | 0.28 |
| Manganese | 2.2 | 0.19 |

The presence or absence of various metallic impurities in the ferrophosphorus anode is not critical for producing organophosphorus compounds by the electrolysis of this invention.

Any suitable indifferent electrical conductor may be employed as the cathode in carrying out the process of the invention. Graphite is preferred as a cathodic material; platinum group metals, silver, gold, or copper may also be used for the cathode.

The cell containing the electrolyte is advantageously constructed of glass or other nonporous ceramic. Other suitable materials of construction are plastics such as polyethylene, polypropylene, polyvinyl chloride, polyvinylidene chloride, cross-linked resins, rubbers, or other materials lined with glass, ceramic, or chemically resistant polymers. The arrangement of the electrodes in the cell is not critical for carrying out the process of the present invention. Various geometric alternatives can be used. For example, two cylindrical electrodes of different size can be placed one inside the other. Or, a straight electrode of any convenient shape can be set inside a cylindrical electrode. Alternatively, two straight, or two paddle-shaped electrodes can be employed.

The electrolysis cell may be compartmented by a separator or uncompartmented without a separator. If a separator is used, it may be a microporous diffusion barrier, that is a diaphragm, such as clay, fused alumina, parchment, cellulosic film, supported water glass, or a textile of asbestos or synthetic fibers. An ionic discriminating barrier, that is a membrane, may be employed such as a synthetic ion-exchange membrane, oxidized cellulosic film, or supported gelatin.

The organic moiety for the organophosphorus compounds produced by the process of the present invention can be supplied by hydroxyl compounds, to make organic phosphates, or sulfhydryl compounds, to make thiophosphates. The hydroxyl compounds can be alcohols, glycols, or phenols. The sulfhydryl compounds can be mercaptans or thiophenols.

Among the alcohols which can be employed in the electrolyte of the present invention to make trialkyl phosphates are the saturated alcohols having 1 to 12 carbon atoms. Among these are methyl, ethyl, isopropyl, propyl, butyl, isobutyl, sec-butyl, amyl, isoamyl, hexyl, cyclohexyl, octyl, capryl, decyl, and lauryl alcohol. Ethylene glycol, 1,2-propanediol, trimethylene glycol, or the butanediols may also be employed as electrolytes.

Among the phenols which can be employed in the electrolyte to make triaryl phosphates are phenol, the cresols, chlorophenols, nitrophenols, bromophenols, and the cyclohexyl phenols. For those phenols which are solids, a liquid electrolyte can be formed by adding an indifferent liquid solvent such as a low-boiling alkane or a liquid aromatic hydrocarbon.

As a source of organosulfur moieties to produce organic thiophosphates mercaptans such as methyl, ethyl, propyl, butyl, amyl, hexyl mercaptan and their isomers may be employed in the electrolyte in practicing the present invention. Aromatic sulfhydryl groups for producing aryl thiophosphates may be supplied by thiophenol, thiocresols, or cyclohexylthiophenol.

The compounds listed above are suggestive of the hydroxyl or sulfhydryl compounds which may be employed in practicing the electrolysis of the present and are not intended to be limiting.

As a source of direct current for the electrolysis a battery or rectifier may be employed. The voltage impressed should be sufficient to electrolyse the hydroxyl or sulfhydryl compound and can range from about 5 volts to about 50 volts, with about 15 volts to about 25 volts preferred. The area of the electrodes, the salt content of the electrolyte, the cell, and the impressed voltage should be so chosen that the current density varies from about 0.001 amp/cm$^2$, with about 0.05 amp/cm$^2$ to about 0.2 amp/cm$^2$ preferred.

In order to make the hydroxyl or sulfhydryl compound ionically conductive, an indifferent ionizable salt should be added to the electrolyte. For this purpose the nonreactive salts of an alkali metal or ammonium cation are preferred. Halogen, nitrate, bicarbonate, bisulfate, or sulfate anions are preferred. Tetramethylammonium chloride is especially preferred as an ion-conductivity agent in the electrolyte. (TMACl).

The examples below illustrate the present invention. Those skilled in the art of organic electrochemistry may conceive of other illustrative alternative modes for practicing this invention which would still be within the scope of this disclosure.

EXAMPLE 1

This example illustrates the preparation of triethyl phosphate.

A cylindrical, jacketed electrolysis cell was constructed of glass 8 cm in diameter and 20 cm high. The jacket had an inlet and outlet for the circulating water used to control the temperature. Approximately 15 cm from the bottom was a fitting for a reflux condenser. A hemispherical, glass top was mounted on the electrolysis cell by means of a ground-glass joint fitted with a number 50, rubber O-ring, through which copper wires connecting to the electrodes were run. Also the top bore an inlet for nitrogen gas. Metal clips held the electrodes suspended from the copper wire leads. A magnetic stirring bar was placed in the bottom of the cell which normally held 350 ml of electrolyte. A direct current rectifier, (Model B-1000, R. O. Hull, Cleveland, Ohio) was the source of power.

The electrolyte was 14.1 g. tetramethylammonium chloride in 310 ml anhydrous ethanol. After purging with nitrogen the electrolysis was carried out at 28° C. for 73 hours with 10 v. D.C. applied, a current varying between 0.1 to 0.38, a, a graphite rod cathode 10 cm long and 0.6 cm in diameter, and a ferrophosphorus (MP) anode, weighing 21.7 g. During the electrolysis the anode lost 9.7 g. weight.

After the electrolysis, a sample of the amber reaction liquor subjected to mass spectrographic analysis showed the presence of both triethyl phosphate and diethylmethyl phosphate. Upon vacuum distillation 29.4 percent of triethyl phosphate was isolated based on the loss of weight of the anode.

EXAMPLE 2

This example illustrates the preparation of tripropyl phosphate directly from ferrophosphorus.

The same equipment and procedure as in Example 1 was used. The electrolyte was 10.9 g. tetramethylammonium chloride in 310 ml n-propanol. After purging with nitrogen the electrolysis was run at 70° C. for 117 hours with 18.5 v. applied voltage, a current of 0.21 a, and a ferrophosphorus (MP) anode, which lost 11.3 g. during the reaction.

After the electrolysis the reaction liquor was stripped of solvent by a rotary vacuum distillation, leaving a tarry residue which was no longer examined. The liquid residue was subjected to a vacuum distillation, leaving a tarry residue which was no longer examined. The liquid residue was subjected to another vacuum distillation. The distillate showed a strong P=O band in infrared spectroscopy, a $^{31}$P nuclear magnetic resonance spectrum similar to that of tripropyl phosphate, and a gas chromatographic spectrum identifying the product as tripropyl phosphate. Disregarding the tarry fraction, the liquid fraction showed 16 percent yield based on weight loss of the anode and 18 percent yield based on current efficiency.

EXAMPLE 3

This example illustrates the preparation of triisopropyl phosphate.

Using the same equipment, electrodes, and procedure as in Examples 1 and 2 an electrolysis was carried out at 40° C. with 11 g. of tetramethylammonium chloride in 310 ml of isopropyl alcohol for 99 hours with 20 v. applied and a current of 0.15 a. The ferrophosphorus anode lost 6.8 g. weight during the electrolysis.

After filtration, stripping the solvent, and vacuum distillation, the product was subjected to infrared spectroscopy, gas chromatography and $^{31}P$ nmr. The predominant product was triisopropyl phosphate with an indication of some phosphonate.

EXAMPLE 4

This example illustrates the use of a bromide as electrolyte.

Following the procedure of the previous examples in the same equipment, two electrolyses were carried out using 7.1 g. sodium bromide in 310 ml anhydrous ethanol as the electrolyte. In each case in addition to triethyl phosphate a significant proportion of triethyl phosphate was produced. Also in both cases the length of the electrolysis was longer than the previous examples. The parameters of these two runs are given below:

|    | Time (hrs) | Voltage | Current (a) | Temp. °C. | % Phosphate | % Phosphite |
|----|------------|---------|-------------|-----------|-------------|-------------|
| 4A | 237        | 11      | 0.12        | 32        | 75          | 25          |
| 4B | 194        | 18.5    | 0.27        | 45        | 85          | 15          |

EXAMPLE 5

This example illustrates other preparations of triethyl phosphate from ethanol by electrolysis with a variety of ferrophosphorus anodes with tetramethylammonium chloride as the electrolytic conductor.

The apparatus of Example 1 was employed with 14.1 g. of the tetramethylammonium chloride in 310 ml anhydrous ethanol. The anode was either a slug of ferrophosphorus melt from a phosphorus furnace or a piece of ore as indicated. The parameters are shown below:

| Run | Anode   | Voltage | Current (a) | Temp. °C. | Time (hrs) | Remarks |
|-----|---------|---------|-------------|-----------|------------|---------|
| 5A  | slug    | 10      | 0.21        | ambient   | 17         | Mass spec. and $^{31}P$ nmr show organophosphate |
| 5B  | slug    | 11      | 0.16        | ambient   | 37         | IR shows organophosphate |
| 5C  | slug    | 10      | 0.26        | 35°       | 80         | triethyl phosphate (TEP) and diethylmethyl phosphate by mass spectroscopy |
| 5D  | ore(MP) | 10      | 0.29        | 37°       | 204        | 30% TEP at 44% current efficiency |
| 5F  | ore(MP) | 18      | 0.33        | 40°       | 83         | 53% TEP at 55% current efficiency |
| 5P  | ore(SB) | 9–25    | 0.04–0.3    | 40°       | 80         | TEP containing a little triethyl |

-continued

| Run | Anode | Voltage | Current (a) | Temp. °C. | Time (hrs) | Remarks |
|-----|-------|---------|-------------|-----------|------------|---------|
|     |       |         |             |           |            | vanadate |

EXAMPLE 6

This example discloses some electrolyses in which the reaction mixture was not completely analyzed to determine the nature of the organophosphorus compound produced.

| Run | Electrolyte | Anode | Voltage | Current (a) | Time (hrs) | Temp. °C. |
|-----|-------------|-------|---------|-------------|------------|-----------|
| 6J  | phenol, TMACl | ore(MP) | 20 | 0.02–0.17 | 3 | 52° |
| 6L  | ethylene glycol, TMACl | slug | 16 | 0.01 | 102 | ambient |
| 6N  | isopropylphenol, TMACl | ore(PMP) | 24 | 0.02 | 195 | 45° |
| 6Q  | neopentyl alc. tetraethylammonium p-toluene sulfonate | ore(MP) | 24 | 0.01–0.04 | 470 | 65° |
| 6S  | ethanol, TMACl | ore(SB) | 13 | 0.04–0.3 | 184 | ambient |
| 6T  | ethanol, sodium cyclopentadeneide in THF | ore(TVA) | 10 | 0.04–0.2 | 5 | 30° |

We claim:

1. A process for the preparation and separation of organophosphorus derivatives of organic hydroxyl or sulfhydryl compounds which includes the step of electrolyzing in a substantially anhydrous medium said organic hydroxyl or sulfhydryl compounds in an electrochemical cell having an anode comprising ferrophosphorus.

2. The process of claim 1 wherein the organic hydroxyl compound is an alcohol.

3. The process of claim 2 wherein the organic alcohol is ethanol.

4. The process of claim 2 wherein the organic alcohol is a propanol.

5. The process of claim 2 wherein the organic alcohol is a butanol.

6. The process of claim 1 wherein the organic hydroxyl compound is a glycol.

7. The process of claim 1 wherein the organic hydroxyl compound is a phenol.

8. The process of claim 1 wherein the organic sulfhydryl compound is a thiophenol.

9. The process of claim 1 wherein the ferrophosphorus contains from about 22 to about 30 weight percent phosphorus.

10. A process for the preparation of organophosphorus derivatives of at least one mercaptan which includes the step of electrolyzing said mercaptan or mixture of mercaptans in an electrochemical cell having an anode comprising ferrophosphorus.

* * * * *

UNITED STATES PATENT AND TRADEMARK OFFICE
CERTIFICATE OF CORRECTION

PATENT NO. : 4,338,166
DATED : July 6, 1982
INVENTOR(S) : Mark A. Kuck et al.

It is certified that error appears in the above-identified patent and that said Letters Patent are hereby corrected as shown below:

Col. 5, line 19, the second "phosphate" should be

-- phosphite --.

Signed and Sealed this

Nineteenth Day of October 1982

[SEAL]

Attest:

GERALD J. MOSSINGHOFF

Attesting Officer

Commissioner of Patents and Trademarks